United States Patent
Park et al.

(10) Patent No.: US 9,835,570 B2
(45) Date of Patent: Dec. 5, 2017

(54) X-RAY DIFFRACTION (XRD) CHARACTERIZATION METHODS FOR SIGMA=3 TWIN DEFECTS IN CUBIC SEMICONDUCTOR (100) WAFERS

(71) Applicant: The United States of America as represented by the Administrator of the National Aeronautics and Space Administration, Washington, DC (US)

(72) Inventors: Yeonjoon Park, Yorktown, VA (US); Hyun Jung Kim, Poquoson, VA (US); Jonathan R. Skuza, Williamsburg, VA (US); Kunik Lee, Fairfax, VA (US); Glen C. King, Williamsburg, VA (US); Sang Hyouk Choi, Poquoson, VA (US)

(73) Assignee: The United States of America as represented by the Administrator of NASA, Washington, DC (US)

( * ) Notice: Subject to any disclaimer, the term of this patent is extended or adjusted under 35 U.S.C. 154(b) by 64 days.

(21) Appl. No.: 14/484,517

(22) Filed: Sep. 12, 2014

(65) Prior Publication Data
US 2015/0078526 A1    Mar. 19, 2015

Related U.S. Application Data

(60) Provisional application No. 61/877,416, filed on Sep. 13, 2013.

(51) Int. Cl.
*G01N 23/207*    (2006.01)
*G01N 23/20*    (2006.01)

(52) U.S. Cl.
CPC ........... *G01N 23/207* (2013.01); *G01N 23/20* (2013.01); *G01N 2223/0566* (2013.01);
(Continued)

(58) Field of Classification Search
CPC ........... G01N 23/20; G01N 2223/0566; G01N 2223/6116; G01N 2223/646; G01N 2223/6462; G01N 23/207
(Continued)

(56) References Cited

U.S. PATENT DOCUMENTS

| | | | | |
|---|---|---|---|---|
| 5,141,569 A | * | 8/1992 | Ito ..................... | H01L 21/02395 148/33 |
| 5,141,893 A | * | 8/1992 | Ito ..................... | H01L 21/02395 117/104 |

(Continued)

OTHER PUBLICATIONS

B. D. Cullity and S. R. Stock. Elements of X-Ray Diffraction, Third Edition (Upper Saddle River, New Jersey: Prentice Hall, 2001), pp. 66-88.*

(Continued)

*Primary Examiner* — Allen C. Ho
(74) *Attorney, Agent, or Firm* — Jennifer L. Riley; Robin W. Edwards; Mark P. Dvorscak

(57) ABSTRACT

An X-ray defraction (XRD) characterization method for sigma=3 twin defects in cubic semiconductor (100) wafers includes a concentration measurement method and a wafer mapping method for any cubic tetrahedral semiconductor wafers including GaAs (100) wafers and Si (100) wafers. The methods use the cubic semiconductor's (004) pole figure in order to detect sigma=3/{111} twin defects. The XRD methods are applicable to any (100) wafers of tetrahedral cubic semiconductors in the diamond structure (Si, Ge, C) and cubic zinc-blend structure (InP, InGaAs, CdTe, ZnSe, and so on) with various growth methods such as Liquid Encapsulated Czochralski (LEC) growth, Molecular Beam Epitaxy (MBE), Organometallic Vapor Phase Epitaxy (OMVPE), Czochralski growth and Metal Organic Chemical Vapor Deposition (MOCVD) growth.

18 Claims, 6 Drawing Sheets
(1 of 6 Drawing Sheet(s) Filed in Color)

(52) U.S. Cl.
CPC ............... *G01N 2223/6116* (2013.01); *G01N 2223/646* (2013.01); *G01N 2223/6462* (2013.01)

(58) Field of Classification Search
USPC ........................................ 378/70, 71, 72, 73
See application file for complete search history.

(56) References Cited

U.S. PATENT DOCUMENTS

| | | | | |
|---|---|---|---|---|
| 5,773,085 | A * | 6/1998 | Inoue | C09K 11/625 117/108 |
| 6,030,595 | A * | 2/2000 | Sumiya | B01J 3/062 423/446 |
| 6,045,614 | A * | 4/2000 | de Lyon | H01L 21/02433 117/100 |
| 6,528,387 | B1 * | 3/2003 | Moriyasu | H01L 21/2007 257/E21.122 |
| 6,768,175 | B1 * | 7/2004 | Morishita | H01L 21/2007 257/347 |
| 6,907,107 | B1 * | 6/2005 | Wallis | G01N 23/207 378/73 |
| 7,049,190 | B2 * | 5/2006 | Takeda | C30B 23/02 257/E21.411 |
| 7,061,010 | B2 * | 6/2006 | Minakata | C30B 7/005 257/40 |
| 7,521,265 | B2 * | 4/2009 | Yokokawa | G01N 23/207 257/E21.521 |
| 7,558,371 | B2 * | 7/2009 | Park | G01N 23/207 378/71 |
| 7,723,814 | B2 * | 5/2010 | Shibasaki | G01R 33/06 257/421 |
| 7,769,135 | B2 * | 8/2010 | Park | G01N 23/207 378/71 |
| 7,906,358 | B2 * | 3/2011 | Park | G01N 23/207 257/614 |
| 8,044,294 | B2 * | 10/2011 | Park | G01N 23/207 136/200 |
| 8,226,767 | B2 * | 7/2012 | Park | G01N 23/207 117/101 |
| 8,257,491 | B2 * | 9/2012 | Park | G01N 23/207 117/1 |
| 8,936,876 | B2 * | 1/2015 | Yamada | H01M 4/587 429/231.8 |
| 8,956,453 | B2 * | 2/2015 | Lieten | C23C 14/06 117/4 |
| 8,962,991 | B2 * | 2/2015 | Jones-Albertus | H01L 31/0687 136/246 |
| 9,082,616 | B2 * | 7/2015 | Merckling | H01L 21/02538 |
| 9,129,808 | B2 * | 9/2015 | Fujii | C30B 25/183 |
| 9,281,427 | B2 * | 3/2016 | Kyono | H01L 31/03523 |

OTHER PUBLICATIONS

Park, Y.; "Analysis of twin defects in GaAs(111)B molecular beam epitaxy growth," Journal of Vacuum Science and Technology B, 2000, 18(3), 1566-1571.
Cohen, D.; McKernan, S.; Carter, C.B., "Characterization of the Absolute Crystal Polarity across Twin Boundaries in Gallium Phosphide Using Convergent-Beam Electron Diffraction," Microscopy and Microanalysis, vol. 5, p. 173-186, 1999.
Park, Y.; King, G.; Choi, S. H., "Rhombohedral epitaxy of cubic SiGe on trigonal c-plane sapphire," Journal of Crystal Growth 2008, 310 (11), 2724-2731.
Cohen, D.; Carter, C.B., "Sigma=, {11(2)over-bar} lateral twin boundaries in GaP," Interface Science 2003, 11.(4), 391-401.
Gerthsen, D; Carter, C.B., "Stacking-Fault Energies of Gaas," Phys Status Solidi A, Applied research, vol. 136, (1), pp. 29-43, 1993.
Gottschalk, H.; Patzer, G.; Alexander, H., "Stacking-fault Energy and Ionicity of Cubic-III-V compounds," Physcia status solidi. a-Applied research, 1978, 45 (1), pp. 207-217.

Bandic, Z.Z., McGill, T.C.; Ikonic, Z., "Electronic Structure of GaN Stacking Faults," Physical Review B, vol. 56, (7), pp. 3564-3566, 1997.
Koguchi, M.; Kakibayashi, H.; Yazawa, M.; Hiruma, K.; Katsuyama, T., "Crystal-Structure Change of GaAs and InAs Whiskers from Zinc-Blende to Wurtzite Type," Jpn. J. Appl. Phys. vol. 31 (1992) pp. 2061-2055, Part 1, No. 7, Jul. 1992.
Latu-Romain, L.; Chaussende, D.; Pons, M., "High-Temperature Nucleation of Cubic Silicon Carbide on (0001) Hexagonal-SiC Nominal Surfaces," Crystal Growth and Design 2006, vol. 6. No. 12, pp. 2788-2794.
Xin, Y.; Brown, P.D.; Duninborkowski, Humphreys, C.J.; Cheng, T.S.; Foxon, C.T., "Microstructural characterisation of GaN(As) films grown on (001) GaP by molecular beam epitaxy," Journal of Crystal Growth, 1997, 171 (3-4), pp. 321-332.
Yoshida, H.; Ikejiri, K.; Sato, T.; Hara, S., Hiruma, K.; Motohisa, J.; Fukui, T , "Analysis of twin defectsin GaAs nanowires and tetrahedra and their correlation of GaAs(111)B surface reconstructions in selective-area metal organic vapour-phase epitaxy," Journal of Crysat Growth 2009, 312 (1), 52-57.
Johansson, J.; Karlsson, L.S.; Dick, K.A.; Bolinsson, J.; Wacaser, B.A.; Deppert, K.; Samuelson, L.,"Effects of Supersatuation on the Crystal Structure of Gold Seeded III-V nanowires," Crystal Growth and Design, 2009, vol. 9, No. 2 , pp. 766-773.
Nishinaga, J.; Takada, T.; Hayashi, T.; Horikoshi, Y., "Crystalline and electrical characteristics of C60-doped GaAs films," Journal of Crystal Growth, 2009, 311 (7), 2232-2235.
Lee, C.H.; Sutono, A.; Han, S.; Lim. K., Pinel, S.; Tentzeris, E.M.; Laskar, J., "A Compact LTCC-Based Ku-Band Transmitter Module," IEEE Transactions on Advanced Packing, vol. 25, No. 3, pp. 374-384. Aug. 2002.
Chang H.Y.; Wang, H.; Yu, M., Shu. Y.H., "A 77-GHz MMIC Power Amplifier for Automotive Radar Applications," IEEE Microwave and Wireless Components Letters, vol. 13, No. 4, pp. 143-145, Apr. 2003.
Kang, D.M., Hong, J.Y., Yoon, H.S.; Lee, K.H.; Choi, I.G., "A Transceiver Module for Automotive Radar Sensors Using W-Band Monolithic Microwave-Integrated Circuit One-Chip Set," Microwave and Optical Technology Letters. vol. 50, No. 9, pp. 2371-2376, Sep. 2008.
Yamamoto, N., Akahane, K., Gozu, S., Ueta, A., and Ohtani, N , "1.55-mu M-Waveband Emissions from Sb-Based Quantum-Dot Vertical-Cavity," Japanese Journal of Applied Physics, vol. 45, No. 4B, 2006, pp. 3423-3426.
Fang, Z-Q, and Look, D.C., "Comparison of deep centers in semi-insulating liquid-encapsulated Czochralski and vertical-gradient freeze GaAs," Journal of Applied Physics, 69 (12), Jun. 15, 1991, pp. 8177-8182.
Fornari, R. Giliolo, E., Mignoni, G., and Masi, M., "A Study of Convection, Striations and Interface Shape in InP Crystals Grown by the Double-Crucible LEC Technique," Cryst. Res. Technol, 32, 1997, 8, pp. 1085-1093.
Joyce, B.A., Shitara, T., Yoshinaga, A., Vvedensky, D. D., et. al., "Elementary processes in the MBE growth of GaAs," Applied Surface Science, 1992, 60-1, pp. 200-209.
Breiland, W. G., Coltrin, M. E., Creighton, J.R., et. al., "Organometallic vapor phase epitaxy (OMVPE)," Materials Science and Engineering, R24 (6) (1999), 241-274.
Weyers, M. Sato, M., and Ando, H., "Red Shift of Photoluminescence and Absorption in Dilute GaAsN Alloy Layers," Japanese Journal of Applied Physics Part 2, No. 7A, Jul. 1, 1992.
Bak-Misiuk, J., Paszkowica, W., Domagala, J., et. al., "Determination of Ga1—xAl xAs epitaxial layer compostion by X-ray intensity measurements of quasi-forbidden reflections," Journal of Crystal Growth 126 (1993), pp. 168-173.
Frymarck, I., Kowalski, G., Kaminska, M., and Krotkus, A., "Structure of GaAs: Be crystals studied by X-ray quasi-forbidden reflections," Journal of Alloys and Compunds 362 (2004), pp. 261-264.
Velling, P., Janssen, G., Agethen, M., Prost, W., and Tegude, F. J., "InGaP/GaAs hole barrier asymmetry determined by (002) X-ray reflections and p-type DB-RTD hole transport," Journal of Crystal Growth 195 (1998), pp. 117-123.

(56) References Cited

OTHER PUBLICATIONS

Marchenko, M.P., Liu, W.G., Badawi, M.H., and Yin, P., "The influence of the scatter of heat flux at the m/c interface on the frequency of appearance of poly body and twin defects during 6" semi-insulating GaAs crystal growth by the VGF method," Journal of Crystal Growth 310 (2008) 2134-2140.

Sajovec, F.; Wolf, R.; Fattah, A.; Bickmann, K.; Wenzl, H.; Nagel, G.; Rufer, H.; Tomzig, E.; Debievre, P., Defect Analysis on Gaas Crystals by Precision-Measurements of Density and Lattice-Parameter. Phys Status Solidi A 1990. 122 (1), pp. 139-152.

* cited by examiner

X-RAY DIFFRACTION (XRD) CHARACTERIZATION METHODS FOR SIGMA=3 TWIN DEFECTS IN CUBIC SEMICONDUCTOR (100) WAFERS

CROSS-REFERENCE TO RELATED PATENT APPLICATION(S)

This patent application claims the benefit of and priority to U.S. Provisional Patent Application No. 61/877,416, entitled "X-RAY DIFFRACTION (XRD) CHARACTERIZATION METHODS FOR SIGMA=3 TWIN DEFECTS IN CUBIC SEMICONDUCTOR (100) WAFERS" filed on Sep. 13, 2013, the contents of which are hereby incorporated by reference in their entirety.

STATEMENT REGARDING FEDERALLY SPONSORED RESEARCH OR DEVELOPMENT

The invention described herein was made in the performance of work under a NASA contract and by employees of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the contractor elected not to retain title.

BACKGROUND OF THE INVENTION

Semiconductor materials are widely utilized in numerous electronic devices. An ingot/boule may be grown from a single seed crystal, and the ingot may be sliced into relatively thin (e.g. 0.75 mm thick) wafers. Various additional processing steps such as deposition, removal, patterning, cutting, doping, etc., may be performed on the wafer to fabricate an electronic device. Various crystal structure defects may be present in semiconductor materials. Such defects may adversely affect the performance of electronic devices made from semiconductor materials.

The 60° rotated twin defect on {111} planes is one of the most common crystal structure defects in many cubic semiconductors. This defect has a sigma=3 grain boundary commonly called the sigma=3 twin defect on {111} plane. It is also called a 180° rotated twin defect because every 120° rotation is identical, due to the threefold symmetry of the cubic [111] direction. Sigma=3 twin defects are also frequently found in the group IV semiconductors (Si, Ge, C) in a diamond structure and other cubic zinc blonde III-V and II-VI compound semiconductors such as GaP, InP, InGaAs, CdTe and ZnSe.

With reference to FIG. 1a, single crystal GaAs 10 comprises gallium atoms 6 and arsenide atoms 8. FIG. 1a shows the single crystal GaAs 10 without defects and FIG. 1b shows the formation of sigma=3/{111} twin defects 12 by a stacking fault 14 on {111} planes adjacent a single crystal GaAs substrate 16. FIG. 1b shows the cubic crystal structure of GaAs and {111} crystal plane normal vectors. The net effect of the sigma=3/{111} twin defect 12 made by a stacking fault 14 is the rotation of the crystal structure cube by 60° while it shares the common triangular {111} plane 20 with the original cube 18 as shown in FIG. 1d.

The low stacking fault formation energy (45 mJ/m² for GaAs (111)), (30 mJ/m for InAs and 17 mJ/m for InP) facilitates frequent creation of sigma=3/{111} twin defects, which become the source of polymorphism between cubic zinc blende structure and hexagonal Wurtzite structure.

Although there have been many nanometer-to-micrometer scale characterizations for the stacking faults and sigma=3 twins using transmission electron microscopy (TEM), only a limited number of wafer-scale macroscopic characterizations such as XRD analysis have been reported. These few reports include an XRD detection method of sigma=3/{111} twin defects on GaAs (111)B wafer and GaAs (111) pole-figure analysis of Carbon-60 induced accidental asymmetric twin defects on GaAs (100) wafer.

Si (100) wafers and GaAs (100) wafers are widely used in the micro-electronics industry. However, known defect measuring techniques (e.g. TEM and Etch-pit density test) damage or destroy the wafer, and the damaged wafer is typically useless after testing. Thus, a non-destructive test to detect/measure sigma=3/{111} defects in various materials would be beneficial.

BRIEF SUMMARY OF THE INVENTION

The present invention comprises non-destructive XRD characterization processes/methods. One aspect of the present invention is a concentration measurement process/method that provides a quality factor (ratio) that quantitatively describes the concentration of sigma=3/{111} twin defects. Another aspect of the present invention is a wafer mapping process/method for any cubic tetrahedral semiconductor wafers including, without limitation, GaAs (100) wafers and Si (100) wafers. The methods/processes of the present invention may utilize (004) pole-figures of cubic semiconductors in order to detect sigma=3/{111} twin defects which are incorporated in (100) wafers during fabrication utilizing processes such as the Vertical Gradient Freeze (VGF) growth of GaAs ingots or Czochralski growth of Silicon ingots. However, it will be understood that the present invention is not limited to semiconductor materials/devices fabricated according to these processes. The XRD methods/processes according to the present invention are applicable to any (100) wafers of other tetrahedral cubic semiconductors in the diamond structure (Si, Ge, C) and cubic zinc-blende structure (InP, InGaAs, CdTe, ZnSe, and so on) with various growth methods including Liquid Encapsulated Czochralski (LEC) growth, Molecular Beam Epitaxy (MBE), Organometallic Vapor Phase Epitaxy (OMYPE), Czochralski growth, Metal Organic Chemical Vapor Deposition (MOCVD) growth, or other processes.

The method/processes of the present invention do not require contact or treatment of the materials being tested. The methods/processes can be utilized to provide a pass/fail (quality factor) measurement of individual wafers in a very short time. Thus, the methods/processes can be utilized in connection with commercial wafer fabrication processes to ensure that the wafers that are produced meet predefined quality/defect criteria. Furthermore, the results of XRD testing/methods/processes according to the present invention can be utilized to identify problems in water fabrication processes whereby the process can be modified to reduce/eliminate defects in the wafers. Significantly, the defect measurement methods/processes of the present invention can be integrated into wafer fabrication processes to provide "real time" feedback that can be utilized to rapidly modify the wafer fabrication process and reduce the number of defective wafers that are fabricated.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
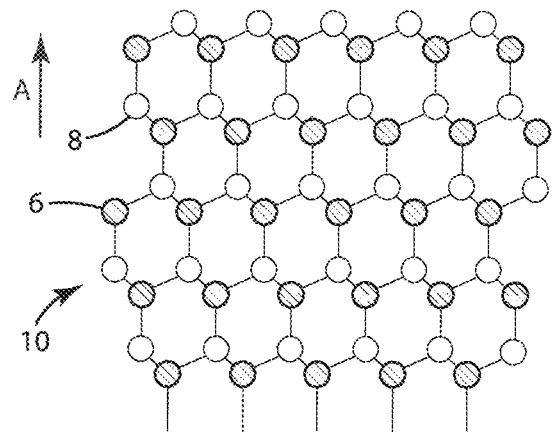
FIG. 1a is a schematic drawing of a single crystal GaAs material.
Figure 1B:
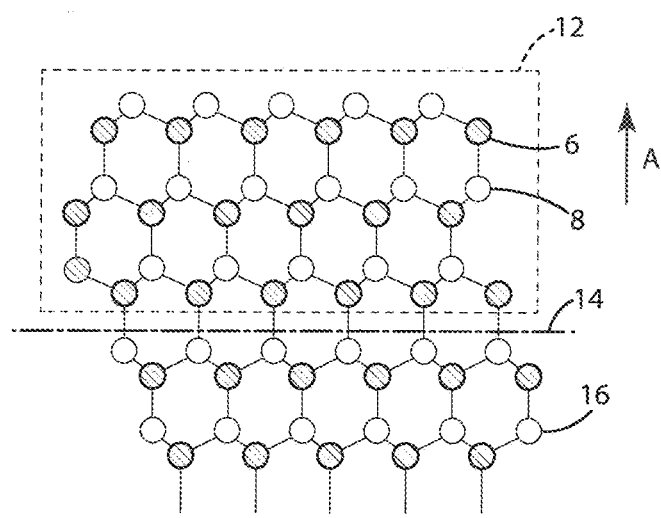
FIG. 1b is a schematic drawing of a single crystal GaAs material showing a stacking fault and sigma=3/{111} twin crystal GaAs.
Figure 1C:
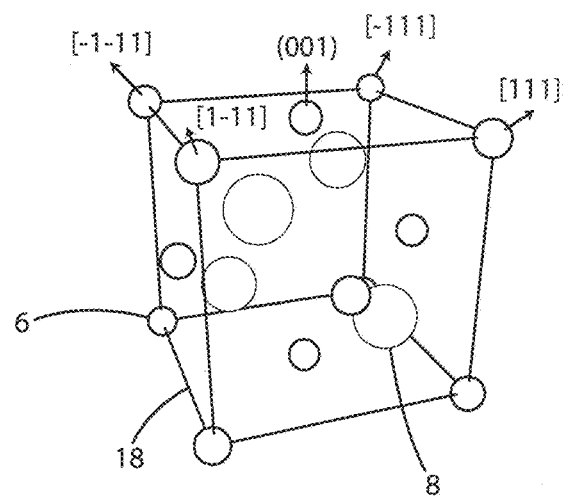
FIG. 1c is a schematic perspective view showing the crystal structure of GaAs.
Figure 1D:
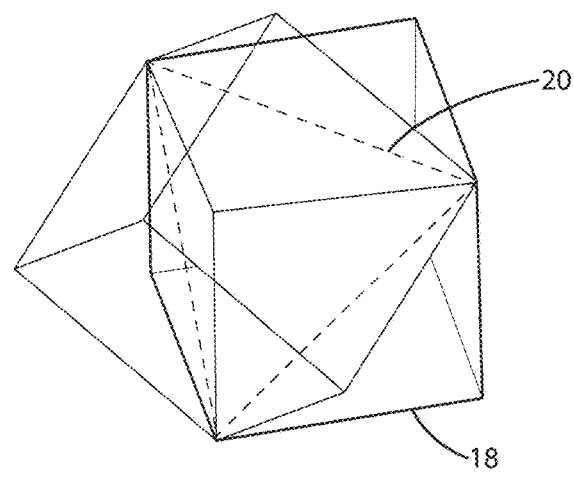
FIG. 1d is a schematic isometric view showing a twin crystal lattice cube rotated by 60° on a (111) plane of the original GaAs cubic lattice.

For purposes of description herein, the terms "upper," "lower," "right," "left," "rear," "front," "vertical," "horizontal," and derivatives thereof shall relate to the invention as oriented in FIGS. 1a and 1b. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As discussed in more detail below, one aspect of the present invention is a process or method for determining a quality factor comprising a ratio as defined in equations 1.0, 1.1, and 1.2 below. The method includes determining the intensity of an original cubic substrate's (004) peak utilizing an XRD process. The XRD process is also utilized to measure the intensity of sigma=3/{111} peaks or spots, as also described in more detail below. The intensity ratio of the sigma=3/{111} defect spots and the original cubic crystals (004) peak defines a quality factor of the semiconductor wafer which is independent from X-ray intensity, slit size and detector sensitivity. This is because the instrumental parameters are compensated in the ratio equation. Thus, the numerical quantity (ratio) provides a quality factor of the wafers in terms of sigma=3/{111} twin defects, in which a lower number signifies fewer sigma=3/{111} defects.

As also described in more detail below, another aspect of the present invention involves an XRD wafer mapping process whereby twin defect density maps of a wafer are developed. The XRD wafer mapping may be utilized to generate a color image using an array/arrangement of one or more colors, each color corresponding to a measured sigma=3/{111} twin defect density, where, for example, red corresponds to a high defect density (FIGS. 4e-4g), and blue represents a low twin defect density. The XRD wafer mapping process can be utilized to determine the propagation of sigma=3/{111} twin defects in an ingot formed utilizing a VGF growth process.

In an exemplary embodiment of the present invention, a GaAs ingot 52 (FIGS. 4d and 4h) was grown utilizing a Vertical Gradient Freezing (VGF) process. The GaAs ingot 52 was sliced to produce multiple 3-inch (100) wafers 50A, 50B, and 50C of 500 micrometer thickness. Each wafer 50A, 50B, 50C was labeled from the conical region 54 adjacent to the single crystal GaAs seed 64 (FIG. 4h) at the bottom 70 to the straight cylindrical upper region 56 where the commercial GaAs (100) wafers are produced. This particular GaAs ingot 52 showed a small portion of a hazy area and a few line defects which propagated through multiple wafers.

A PANalytical X'Pert Pro MRD X-ray diffractometer (not shown) with a 4-circle high resolution goniometer in the Bragg-Brentano configuration was used to characterize the GaAs wafers 50A, 50B, and 50C. The X-ray source was Cu Kα lines with an average wavelength of 1.54187 Å which were filtered by a parabolic X-ray mirror crystal monochromater. The intensity ratio of Cu Kα/Cu kα was 0.5. A line X-ray source with a parabolic mirror was used for the 2θ-Ω scan and a point X-ray source with a beam mask (not shown) was used for the pole figure measurement and the defect wafer mapping. In the 2θ-Ω scan, a 0.02 mm nickel filter and ¼° divergence slit were used for the incidence beam optics and 1/16° receiving slit and ¼° anti-scatter slit were used for the diffracted beam optics.

For the pole figure measurement, a Soller slit of 0.04 radian with a 10 mm beam mask and 2° divergence slit were used for the incidence beam optics and ¼° receiving slit and ½° anti-scatter slit were used for the diffracted beam optics. For the (004) pole figure, 2θ was set to 66.0987° and Ω was set to 33.1141° for the maximum intensity. The in-plane rotation (angle Φ) scan was made in the range of 0°-360° with 3° step and the tilt angle (angle Ψ) scan was made from 0° to 90" with 3° steps.

Wafer defect mapping (FIGS. 4e-4g) was made with XY movement of the sample stage in 0.5 mm steps. A 5 mm beam mask and 1° divergence slit were used for the incidence beam optics and 0.04 radian Soller slit with ½° receiving slit and 1° anti-scatter slit were used for the diffracted beam optics. PANalytical X'pert Data Collector software was used for acquisition of the X-ray diffraction data. The pole figure and wafer mapping were analyzed with X'pert Texture software and X'pert Epitaxy software, respectively.

Pole Figure Analysis

Figure 2:
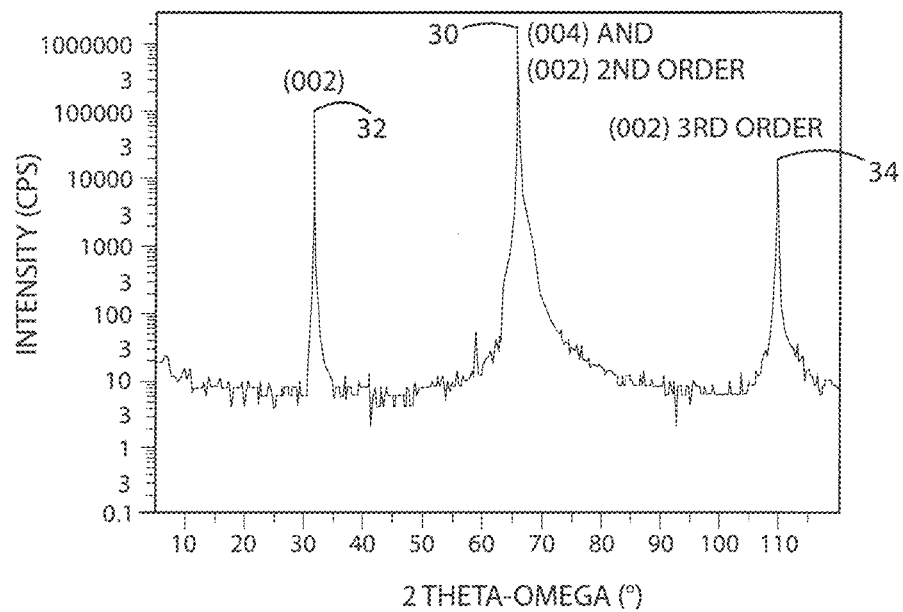
FIG. 2 is a graph showing XRD 2θ-Ω normal scan of a GaAs wafer.

FIG. 2 is a logarithmic Y-scale plot of the 2θ-Ω XRD normal scan of a GaAs (100) wafer which shows (hkl) peaks in the [001] direction (i.e. the surface normal direction). The strongest (004) peak 30 is located at 2θ=66.039° with an intensity of 1,742,878 counts per second (cps) with the overlap of the $2^{nd}$ order peak of quasi-forbidden (002) plane. The first order (002) peak 32 is located at 2θ=31.618° with an intensity of 99,217 cps and the third order (002) peak 34 is located at 2θ=109.670° with an intensity of 18,505 cps. The third order (002) peak 34 is often called the (006) peak although there is no actual atomic plane at ⅙ of the vertical lattice constant. The quasi-forbidden GaAs (002) peaks appear in many XRD reports as a result of the lattice strain and defects. The 2θ-Ω XRD normal scan of FIG. 2 with the very strong (004) peak 30, the weak (002) 32, 34 and no other peaks shows that this VGF grown GaAs wafer exhibits commercial grade mono-crystalline quality.

Figures 3A, 3B:
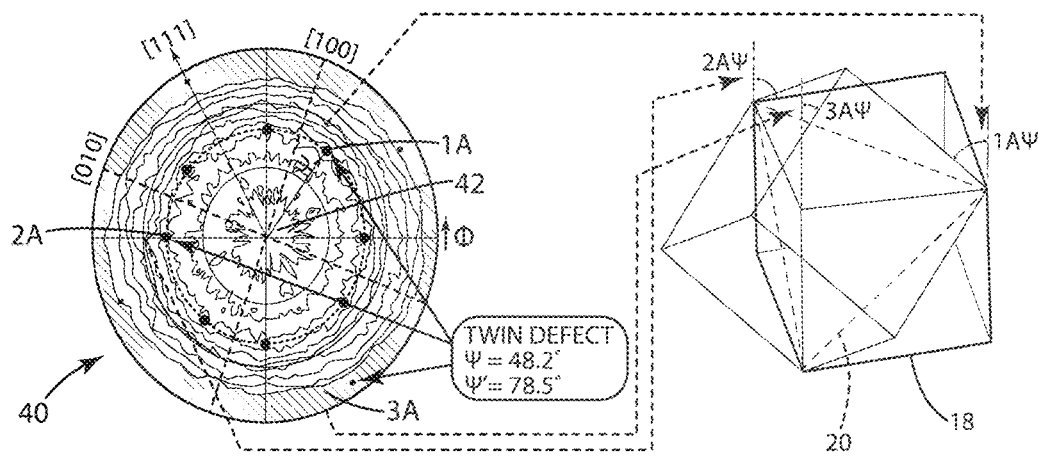
FIG. 3a is pole-figure of GaAs (004) intensity (CPS)
FIG. 3b is a schematic isometric view showing the angles of the sigma=3/{111} twin defects with respect to the original crystal.

The pole figure of GaAs (004) plane diffraction is plotted in FIG. 3a. The pole figured 40 is made in a logarithmic intensity scale with a polar coordinate (radius ψ=tilt angle) of the in-plane rotation angle Φ for the water rotation (0° to 360°) and the radius ψ for the wafer tilt angle (0° to 90°) in order to reveal the weak twin defect peaks. The single crystal GaAs (004) peak 42 is located at the center of the pole-figure with a very strong intensity of 1,289,770 cps. At the tilt angle ψ=48.2°, eight small spots 1A, 2A which are usually called peaks in XRD-scans appear in a generally symmetric pattern. At another tilt ψ=78.5°, four weak peaks 3A appear every 90°. These 12 peaks, i.e. 8 peaks at ψ=48.2° and 4 peaks at ψ=78.5° are {004} peaks of sigma=3/{111}) twin defects. The angular relationships of the crystal planes are shown in FIG. 3b. Three inter-planar angles of 1A(ψ), 2A(ψ) and 3A (φ) with respect to the vertical c-axis direction in FIG. 3b are assigned to three twin defect peaks, 1A and 2A at the same angle ψ=48.2° and 34A at v=78.5° from the center 42 of the pole FIG. 40, i.e. [004] direction in FIG. 3a.

The vertical tilt angles and projected in-plane rotation angles in the XY plane between the twin's [004] plane and the original single crystal GaAs [100] and [110] directions are listed below.

For angle 1A in FIG. 3b

In-plane rotation angle (ΔΦ) between twin's [004] direction and original single crystal's [100] direction=−26.57°, Vertical tilt angle (Δψ) between twin's [004] direction and original single crystal's [004] direction=48.2°.

For angle 2A in FIG. 3b

In-plane rotation angle (ΔΦ) between twin's [004] direction and original single crystal's [010] direction=+26.57°, Vertical tilt angle (Δψ) between twin's [004] direction and original single crystal's [004] direction=48.2°.

For angle 3A in FIG. 2b,

In-plane rotation angle (ΔΦ') between twin's [004] 3A direction and original single crystal's [110] direction=180°, Vertical tilt angle (Δψ) between twin's [004] 3A direction and original single crystal's [004] direction=78.5°.

Therefore, four {±1, ±1, 1} corner planes on a (100) wafer makes (4 planes under 90° rotation)×(3 twin peaks per plane)=12 twin defect peaks, of which 8 peaks are at ψ=48.2 and 4 peaks at ψ'=78.5° in the (004) pole FIG. 40 of FIG. 3a. The intensity of the twin defect peaks 1A and 2A at ψ=48.2° are 3,459 cps and 4,276 cps, respectively and that of the third peak 3A is 817 cps. The intensity of the peaks in the pole Figure decreases as the tilt angle ψ increases because the X-ray beam passing through and returning from the material is strongly attenuated due to the longer beam path near the glancing exit angle at the higher tilt angle. The ratio of averaged height intensity (magnitude) of twin's {004} peaks 1A and 2A, divided by the height intensity (magnitude) of the original single crystals (004) peak is $$\frac{(3{,}459 + 4{,}276)/2}{1{,}289{,}770} = 0.0030 = 0.30\%,$$

which means that the concentration of sigma=3/{111} twin defects is small but detectable with XRD methods/processes according to the present invention.

XRD Wafer Mapping

Figure 4A:
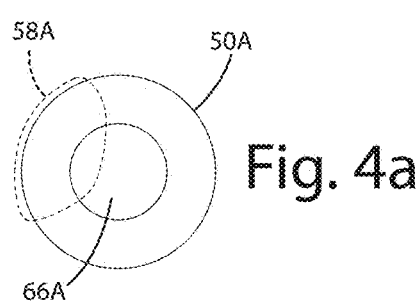
FIG. 4a is a plan view of a conical semiconductor wafer specimen cut from the GaAs ingot of FIG. 4d.
Figure 4B:
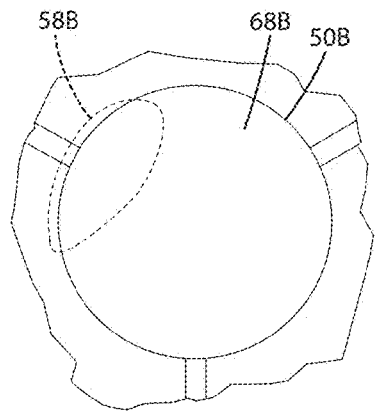
FIG. 4b is a plan view of a cylindrical semiconductor wafer specimen cut from the GaAs ingot of FIG. 4d.

A wafer mapping XRD scan was made using the twin defect's (004) peak 1A in FIG. 3a. After aligning the wafer angles (Ω, ψ, Φ) and the detector angle (2θ) to the twin defect's (004) peak 1A with a beam mask, the sample stage was moved in the XY direction in 0.5 mm steps. FIGS. 4a, 4b, and 4c show GaAs wafers 50A, 50B, and 50C, respectively. With further reference to FIG. 4d, the wafers 50A, 50B, and 50C were cut from different sections of a VGF grown GaAs ingot 52. Wafer 50A comprises a conical sample cut from conical portion 54 of GaAs ingot 52 (FIG. 4d), and wafers 50B and 50C comprise cylindrical wafers cut from straight cylindrical upper region 56 of GaAs ingot 52.

Figure 4E:
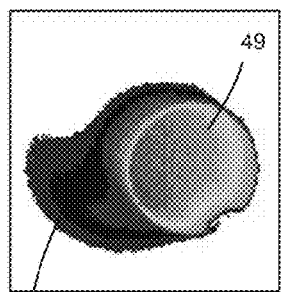
FIG. 4e is a colored image of twin defect wafer mapping results corresponding to the wafer of FIG. 4a wherein red color has the highest defect density (0.3% by intensity ratio) through yellow and green, to blue (lowest intensity ratio)
Figure 4F:
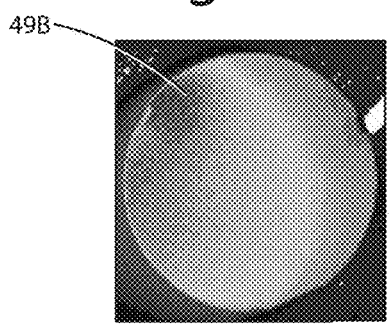
FIG. 4f is a colored image of twin defect wafer mapping results corresponding to the wafer of FIG. 4h wherein red color has the highest defect density (0.3% by intensity ratio) through yellow and green, to blue (lowest intensity ratio)
Figure 4C:
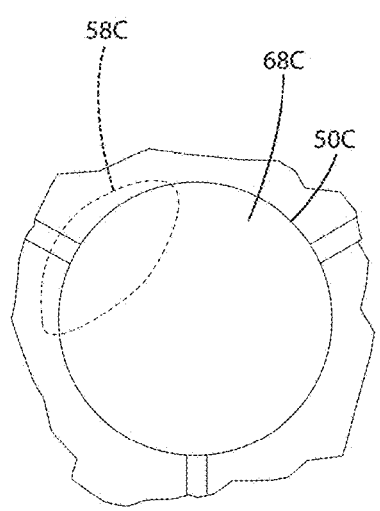
FIG. 4c is a plan view of a cylindrical semiconductor wafer specimen cut from the GaAs ingot of FIG. 4d.
Figure 4G:
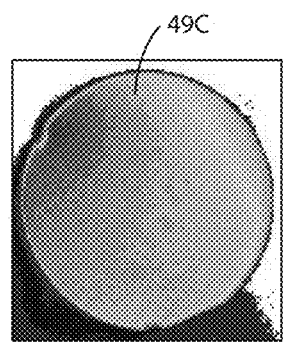
FIG. 4g is a colored image of twin defect wafer mapping results corresponding to the wafer of FIG. 4c wherein red color has the highest defect density (0.3% by intensity ratio) through yellow and green, to blue (lowest intensity ratio)
Figure 4D:
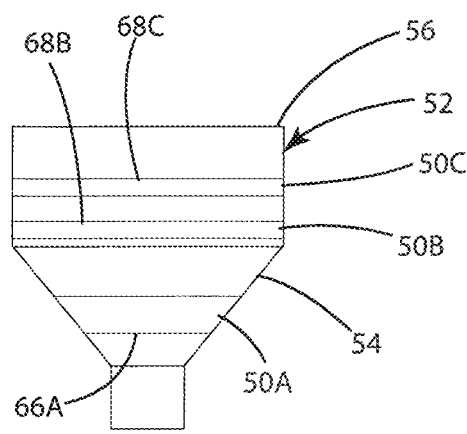
FIG. 4d is a side elevational view of a GaAs ingot grown utilizing a VGF process.

FIGS. 4e-4g are twin defect density maps (color) corresponding to FIGS. 4a-4c, respectively. Regions 58A-58C (FIGS. 4a-4c) have relatively high sigma=3/{111} twin defects. Regions 58A-58C generally correspond to the red regions 49, 49B, 49C, respectively, of FIGS. 4c-4g. In FIGS. 4e-4g, the color red has the highest defect density (0.3% by intensity ratio) followed by yellow and green, to blue (lowest intensity ratio). However, it will be understood that this is merely an example of a suitable mapping arrangement and the present invention is not limited to this example.

The conical wafer 50A was measured using the planar bottom surface 66A which is close to the single crystal GaAs seed 64 (FIG. 4h) utilized in the VGF growth process. The other wafers 50B and 50C were measured using the top surfaces 68B and 68C, respectively. The drawing and wafer mapping result (FIG. 4c) of the bottom surface 66A of conical wafer 50A is flipped horizontally in order to provide the same orientation with respect to other wafers' top surfaces. Because the conical wafer 50A has a slope with a tall thickness, the XRD wafer mapping (FIG. 4e) shows a background tail area 48 in the boundary where the wafer height deviates from the XRD focal point. The flat circular (center) area 49 (FIG. 4e) shows the correct XRD twin defect mapping result corresponding to the flat circular bottom surface 66A (FIG. 4a). The orientation of the pole figure in FIG. 3a and the XRD twin defect wafer mapping results in FIGS. 4e-4g are aligned in the same direction. The red color (FIG. 4e) shows that there is high density of twin defects in the left side (FIGS. 4a and 4e) of the conical wafer 50A. The high defect region 76 (FIG. 4h) extends/propagates to the top left corners of upper wafers 50B and 50C, which is the [111] direction of the GaAs wafer in FIG. 3a.

Figure 4H:
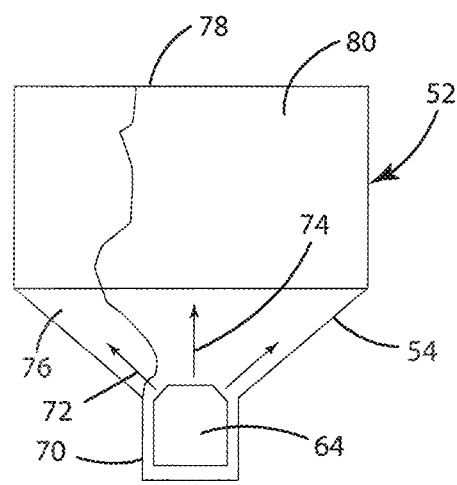
FIG. 4h is a side elevational view of the GaAs ingot of FIG. 4d showing a single crystalline seed and propagation of the twin defect along the {111} direction.

With reference to FIG. 4h, propagation of the sigma=3/ {111} twin defects along [111] direction can be explained as follows. In the VGF growth of a GaAs ingot 52, a small single crystal seed 64 is positioned at the bottom 70 under the conical region 54. Very careful thermal controls are applied in order to regulate the crystallization velocity as the GaAs ingot 52 is formed. Arrows 72 and 74 represent the (111) and (100) planes, respectively of the crystal seed 64. During the vertical freezing process, {111} facet planes can be created accidentally or natively from the seed crystal's {111} facets. Also, the VGF growth inside the conical region 54 requires the expansion of the GaAs crystal into the side directions including <111> directions. Therefore, it is very easy to create sigma=3/{111} twin defects on the {111} facets due to the low formation energy in such a growth condition. Once the twin defect is created, it propagates to the upper wafer regions vertically as the GaAs ingot 52 grows to form a high defect region 76 having high twin defect density/frequency. A boundary 78 extends between high defect region 76 and low defect region 80.

Figure 5:
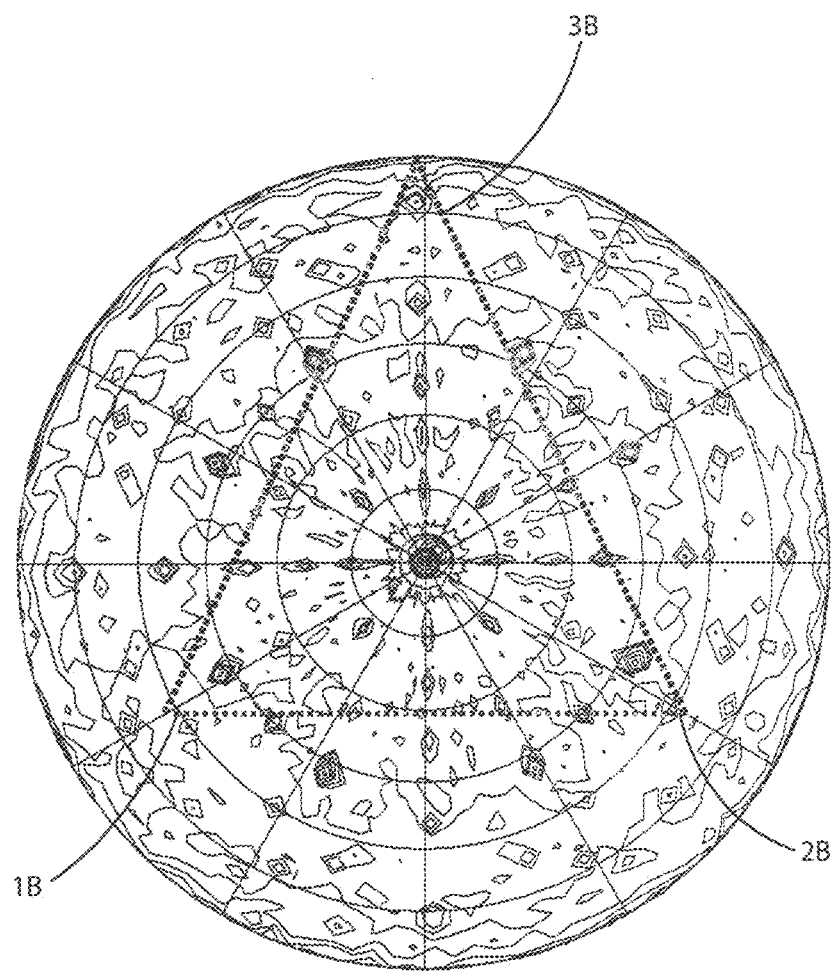
FIG. 5 is a (004) pole figure of a silicon (100) wafer, test grade, P-type 0-100 Ohm·Cm.

According to another exemplary embodiment of the present invention, a Czochralski grown commercial grade Silicon (100) wafer was tested utilizing substantially the same X-ray diffraction methods as described above in connection with FIGS. 4a-4h. The silicon wafer (not shown) was mounted on the XRD sample holder with a slightly different in-plane angle from GaAs wafer alignment. The pole-figure analysis for the silicon (100) wafer is shown in FIG. 5. Substantially, the same sigma=3/{111} twin defect peaks are shown for the silicon (100) wafer (FIG. 5) as for the GaAs wafer (FIG. 3a). Thus, the positions of peaks 1B, 2B, and 3B (FIG. 5) are substantially the same as peaks 1A, 2A, 3A, respectively (FIG. 3a) of the GaAs (100) wafer case described above. The vertical tilt angle of sigma=3/Si(100) peaks 1B and 2B are 48.2°, which is the same as the peaks 1A and 2A of GaAs (100) wafer's sigma=3 defect. The vertical tilt angle of peak 3B in FIG. 5 is 780, which is the same vertical tilt angle as the peak 3A of GaAs (100) case in FIG. 3. The Si(100) wafer sigma=3 defect's in-plane angles between the 1B, 2B and 3B peaks in FIG. 5 are the same as those of the 1A, 2A and 3A peaks, respectively, of the GaAs (100) wafer described above (FIG. 3a). This particular Si(100) wafer contains many smaller peaks which are different from the sigma=3/{111} twin defect peaks. These smaller peaks may represent other polycrystalline defects, such as low angle twin defects on (110) plane.

The important eight strong spots at 48.2° vertical tilt angle and four weak spots at 78.5° vertical tilt angle are detected in both GaAs (100) wafer and Si(100) wafer. These total 12 spots in FIG. 3 and FIG. 5 came from [4-upper corners, i.e. {111} planes of Si/GaAs (100) cubic crystal]×[3 facets of sigma=3/{111} defects per corner]=12 peaks in the XRD pole figures of FIGS. 3a and 5.

Thus, according to the exemplary embodiments described above, the present invention comprises at least two systematic X-ray diffraction (XRD) processes/methods that may be utilized to characterize sigma=3/{111} twin defects on VGF grown mono-crystalline GaAs (100) wafers and Czochralski grown Si (100) wafers. The XRD analysis of GaAs and Si (004) pole figures reveals information about the total concentration and orientation distribution of the twin defects. The XRD wafer mapping method shows the spatial distribution of the twin defects. XRD analysis of multiple sequential wafers from the same ingot reveals the defect formation and propagation mechanisms.

XRD methods/processes according to the present invention are applicable to all mono-crystalline tetrahedral cubic semiconductor wafers including group IV semiconductors in a diamond structure and group III-V & II-VI semiconductors in a cubic zinc-blende structure. The fabrication of monocrystalline semiconductor wafers and epitaxial thin films in various fields of industry may be improved utilizing methods/processes according to the present invention.

The methods/processes of the present invention provide unique solutions that can be utilized to characterize sigma=3 twin defects in (100) wafers and ingots. For example, the intensity of sigma=3/{111} spots, such as peak volume (height×tilt-angle)×in-plane angle), peak area (height)×tilt angle or height×in-plane angle), or peak height can be measured, and the numerical data can be used as a standard parameter to evaluate the quality of a wafer. If the intensity of the original cubic substrate's (004) peak is also measured, the intensity ratio of sigma=3/{111} defect spots and original cubic crystal's (004) peak may comprise a quality factor of the wafer Which is independent from X-ray intensity, slit size and detector sensitivity because the instrumental parameters are compensated in the ratio equation. Therefore, the following numerical quantity (intensity ratio) may serve as a quality factor of the wafers in terms of sigma=3 twin defects, in which a lower number indicates that there are fewer sigma=3 defects. This number (intensity ratio) can be used as an industrial standard to indicate the quality of a wafer.

(1) Quality Factors with Instrumental Dependence Such as X-Ray Intensity, Slit Size, Detector Sensitivity:

1. Absolute intensity of sigma=3/{111} spots in XRD scan including (004) pole figure, tilt-angle vs. intensity scan, in-plane angle vs. intensity scan, tilt-angle vs. in-plane angle vs. intensity, omega-scan around 48.2° or 78.5° tilt angle and in-plane angle, detector angle (2-theta) scan around 48.2° or 78.5° tilt angle and in-plane angle and two-theta—omega scan around 48.2° or 78.5° tilt angle and in-plane angle.

(2) Quality Factors Independent From XRD Instrument Parameters:

2. Intensity ratio of sigma=3/{111} spots and original substrate's (004) peak $$\text{Ratio 1} = \frac{\text{Average intensity of sigma} = 3 \text{ spots}}{\text{Substrate's(004)peak intensity}} \quad (1.0)$$

$$\text{Ratio 2} = \frac{\text{Intensity of one of sigma} = 3 \text{ spots}}{\text{Substrate's(004)peak intensity}} \quad (1.1)$$

$$\text{Ratio 3} = \frac{\text{Combination of sigma} = 3 \text{ spots}}{\text{Substrate's(004)peak intensity}} \quad (1.2)$$

Sigma=3 spots/peaks can be selected from eight spots/peaks at 48.2° tilt angle or four spots/peaks at 78.5°. Eight spots/peaks at 48.2° tilt angle are stronger than those at 78.5°. Therefore, it may be preferable to use the eight strong spots/peaks at 48.2° tilt angle to measure the quality factor (ratio). The magnitude of the intensities for the ratios 1-3 above can be measured with a conventional X-ray diffraction machine with one or two scanning detectors and a rotating sample goniometer.

The quality factor(s) (Ratios 1-3) can also be measured with multiple fixed detectors which are installed at predefined angles rather than scanning and rotating the wafers. If the wafer is loaded with the same in-plane angle every time, the detectors located at predefined angles are capable of measuring the quality factor much faster than scanning the angles with one detector. The actual density of sigma=3/{111} defect can be calculated from the quality factor (Ratios 1-3) with a proportional coefficient.

In general, all three Ratios may be utilized to define a quality factor. Alternatively, a single ratio may be utilized to define a quality factor, or any combination of Ratios 1-3 may be utilized to define a quality factor.

(3) Wafer Mapping Method for Sigma=3/{111} Twin Defect on (100) Wafers

The detector and sample angles are aligned with 48.2° tilt angle and one of the eight peaks/spots' in-plane angles. For the best spatial resolution, a beam mask is inserted in front of the X-ray source to form a narrow focused beam. The wafer is moved in the X-Y directions (i.e. the X-Y plane), and the instrument measures the intensity of the diffracted beam resulting from the sigma=3 twin defects. The instrument creates a map of the concentration of sigma=3 twin defects by showing the intensity of the refracted beam at each (X, Y) coordinate.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." As used herein, the term "and/or" includes any and all combinations of one or more of the associated listed items. As also used herein, the term "combinations thereof" includes combinations having at least one of the associated listed items, wherein, the combination can further include additional, like non-listed items. Further, the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

Reference throughout the specification to "another embodiment", "an embodiment", "exemplary embodiments", and so forth, means that a particular element (e.g., feature, structure, and/or characteristic) described in connection with the embodiment is included in at least one embodiment described herein, and can or cannot be present in other embodiments. In addition, it is to be understood that the described elements can be combined in any suitable manner in the various embodiments and are not limited to the specific combination in which they are discussed.

What is claimed is:

1. A method of characterizing sigma=3 twin defects on {111} planes of semiconductor materials, the method comprising:
   utilizing an X-ray diffraction (XRD) process to measure a magnitude of a (004) intensity peak of a semiconductor material specimen;
   utilizing the X-ray diffraction (XRD) process to measure a magnitude of at least one twin defect intensity peak of the semiconductor material specimen; and
   determining a quality factor ratio by dividing the magnitude of the at least one of the twin defect intensity peak by the magnitude of the (004) intensity peak.

2. The method of claim 1, further including:
   measuring the magnitudes of a plurality of twin defect intensity peaks of the semiconductor material specimen;
   determining an average twin defect intensity peak by dividing a sum of the magnitudes of the plurality of twin defect intensity peaks by the number of twin defect intensity peaks; and
   determining a quality factor ratio by dividing the average twin defect intensity peak by the magnitude of the (004) intensity peak.

3. The method of claim 2, wherein:
   the at least one twin defect intensity peak of the semiconductor material specimen includes eight discrete twin defect intensity peaks at a tilt angle of about 48°.

4. The method of claim 3, wherein:
   determining the quality factor ratio includes determining an average twin defect intensity peak by dividing a sum of the magnitudes of the eight discrete twin defect intensity peaks by eight.

5. The method of claim 2, wherein:
   the at least one twin defect intensity peak of the semiconductor material specimen includes four discrete twin defect intensity peaks at a tilt angle of about 78.5°.

6. The method of claim 5, wherein:
   determining the quality factor ratio includes determining an average twin defect intensity peak by dividing a sum of the magnitudes of the four discrete twin defect intensity peaks by four.

7. The method of claim 1, wherein:
   utilizing the X-ray diffraction (XRD) process to measure a magnitude of at least one twin defect intensity peak of the semiconductor material specimen that includes measuring a plurality of twin defect intensity peaks of the semiconductor material specimen by scanning and rotating the semiconductor material specimen.

8. The method of claim 1, wherein:
   utilizing the X-ray diffraction (XRD) process to measure a magnitude of at least one twin defect intensity peak of the semiconductor material specimen that includes measuring a plurality of twin defect intensity peaks of the semiconductor material specimen with a plurality of fixed detectors disposed at predefined angles relative to the semiconductor material specimen.

9. The method of claim 1, wherein:
   the semiconductor material specimen comprises a GaAs wafer.

10. The method of claim 1, wherein:
    the semiconductor material specimen comprises a silicon wafer.

11. The method of claim 1, further including:
    determining an actual density of sigma=3/{111} defects utilizing a proportional coefficient.

12. A method of mapping sigma=3/{111} twin defects of a specimen comprising (100) semiconductor material utilizing an X-ray diffraction (XRD) process, the method comprising:
    determining a first tilt angle at which a plurality of peak intensities occurs due to sigma=3/{111} twin defects in a (100) semiconductor material of the specimen;
    aligning a detector angle and a sample angle with the first title angle and an in-plane angle of a selected intensity peak of sigma=3/{111} defects;
    moving the specimen in a first plane relative to a detector while measuring the intensity of a diffracted x-ray beam corresponding to a density of sigma=3/{111} twin defects utilizing the detector to provide sigma=3/{111} intensity data for a plurality of pairs of coordinates in the first plane; and forming a map showing sigma=3/{111} twin defect intensity at a plurality of pairs of coordinates in the first place.

13. The method of claim 12, wherein:
the first tilt angle is about 48.2°.

14. The method of claim 13, wherein:
the first plane comprises an X-Y plane, and moving the specimen in the first plane relative to the detector comprises moving the specimen in the X-Y plane.

15. The method of claim 14, wherein:
the map comprises a plurality of colors corresponding to a plurality of measured sigma=3/{111} twin defect densities.

16. A method of using X-ray diffraction (XRD) to characterize sigma=3/{111} twin defects in a semiconductor (100) specimen, the method comprising:
utilizing an X-ray diffraction (XRD) process to measure magnitudes of a plurality of intensity peaks of a diffracted beam corresponding to sigma=3/{111} twin defects at a first vertical tilt angle between a [004] direction of an original single crystal of a semiconductor (100) defect of the semiconductor (100) specimen at a plurality of in-plane rotation angles;
comparing the magnitude of at least one intensity peak corresponding to sigma=3/{111} twin defects to the magnitude of an intensity peak of a diffracted beam corresponding to the [004] direction of an original single crystal of the semiconductor (100) specimen.

17. The method of claim 16, wherein:
the semiconductor (100) specimen comprises GaAs.

18. The method of claim 16, further including:
dividing the magnitude of at least one sigma=3/{111} intensity peak by the magnitude of the intensity peak at the [004] direction.

* * * * *